US00PP07906P

United States Patent [19]

Warriner

[11] Patent Number: Plant 7,906

[45] Date of Patent: Jul. 14, 1992

[54] ROSE PLANT JACDRIFT

[75] Inventor: William A. Warriner, Tustin, Calif.

[73] Assignee: Bear Creek Gardens, Inc., Medford, Oreg.

[21] Appl. No.: 625,991

[22] Filed: Dec. 10, 1990

[51] Int. Cl.[5] ..... A01H 5/00
[52] U.S. Cl. ..... Plt./8.1
[58] Field of Search ..... Plt. 7, 8

*Primary Examiner*—Howard J. Locker
*Attorney, Agent, or Firm*—Klarquist, Sparkman, Campbell, Leigh and Whinston

[57] ABSTRACT

A miniature class rose plant having low compact dwarf spreading habit of growth, profusion of small white flowers in large clusters, dark green glossy foliage, resistance to rust and powdery mildew, ease of propagation by softwood cuttings and pleasant scent.

1 Drawing Sheet

1

The present invention relates to a new and distinct variety of rose plant of the miniature class which was originated by me by crossing the variety Petticoat, U.S. Plant Pat. No. 5,039, with the variety Orange Honey, U.S. Plant Pat. No. 4,496.

The primary objective of this breeding was to produce a new rose variety having the spreading low growing habit of both Petticoat and Orange Honey but with the superior dark green, disease-resistant foliage of Petticoat, the fragrance of Orange Honey and the flower size of Petticoat. The objective was substantially achieved along with other desirable improvements as evidenced by the following unique combination of characteristics which are outstanding in the new variety and which distinguish it from its parents, as well as from all other varieties of which I am aware:

1. Low, compact dwarf spreading habit of growth.
2. Profusion of small white flowers in large clusters.
3. Dark green, glossy foliage.
4. Resistance to rust and powdery mildew.
5. Ease of propagation by softwood cuttings.
6. Pleasant scent.

Asexual reproduction of this new variety by softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Petticoat, U.S. Plant Pat. No. 5,039.

*Pollen parent.*—Orange Honey, U.S. Plant Pat. No. 4,496.

Classification:

*Botanical.*—Rosa hybrida.

*Commercial.*—Miniature.

2

FLOWER

Observation made from specimens grown in a garden in Somis, Calif. in September, 1990.

Blooming habit: Continuous.

Bud:

*Size.*—$\frac{1}{2}$ to $\frac{3}{4}$ inches when the petals start to unfurl.

*Form.*—Short, pointed ovoid.

*Color.*—When sepals first divide, bud color is Yellow White Group 158B. When half blown, the upper sides of the petals are White Group 155D; and the lower sides of the petals are White Group 155D.

*Sepals.*—Color: Green Group 139C. Surface texture: Covered with fine hairs. There are three lightly appendaged sepals. There are two unappendaged sepals with hairy edges.

*Receptacle.*—Color: Green Group 141C. Shape: Apple. Size: Small ($\frac{1}{4}'' \times \frac{1}{4}''$). Surface: Hairy.

*Peduncle.*—Length: Short (2"). Surface: Smooth with some very fine hairs. Color: Light green with some bronze cast. Strength: Stiff, slender.

Bloom:

*Size.*—Small. Average open size is 2–$2\frac{1}{4}$ inches.

*Borne.*—Several together in pyramidal clusters.

*Stems.*—Short, strong.

*Form.*—When first open: Cupped. Permanence: Flattens.

*Petalage.*—Number of petals under normal conditions: 20.

*Color.*—The upper side of the petals is White Group 155D. The reverse side of the petals is White Group 155D. The base of each petal has a small yellowish half moon at the point of attachment ($1/16'' \times 1/16''$). The major color on the upper side is White Group 155D.

*Variegations.*—None.

*Discoloration.*—No general tonality change at the end of the first day. No change at the end of the third day.

*Fragrance.*—Moderate.

Petals:

*Texture.*—Thick.

*Shape.*—Notched and deltoid.

*Form.*—Flat.

*Arrangement.*—Imbricated, with few petaloids in the center.

*Persistence.*—Drop off cleanly.

*Lastingness.*—On the plant: Fair (3 to 5 days). As a cut flower: Fair (3 to 5 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Vigorous, dwarf, sprawling, compact. 14" to 18" tall×30" wide as grown in Somis, Calif.

Foliage: Number of leaflets on normal mid-stem leaves: 5 with 2 occasional very small additional leaflets.

*Size.*—Small (2½"×1½").

*Quantity.*—Normal.

*Color.*—New foliage: Reddish. Old foliage: Dark green, glossy.

Leaflets:

*Shape.*—Pointed oval.

*Texture.*—Upper side: Leathery, glossy, smooth.

*Edge.*—Serrated.

*Serration.*—Single, small.

*Petiole rachis.*—Color: Reddish.

*Petiole underside.*—Smooth with occasional very small prickles.

*Stipules.*—Short (¼") bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—Ordinary quantity on main canes from base and on laterals from main canes.

*Form.*—Short, straight to hooked slightly downward.

*Color when young.*—Red.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its low compact dwarf and spreading habit of growth, its constant and abundant production of pure white flowers, its dark green, glossy and very healthy foliage, its ease of propagation by softwood cuttings and its pleasant fragrance.

* * * * *

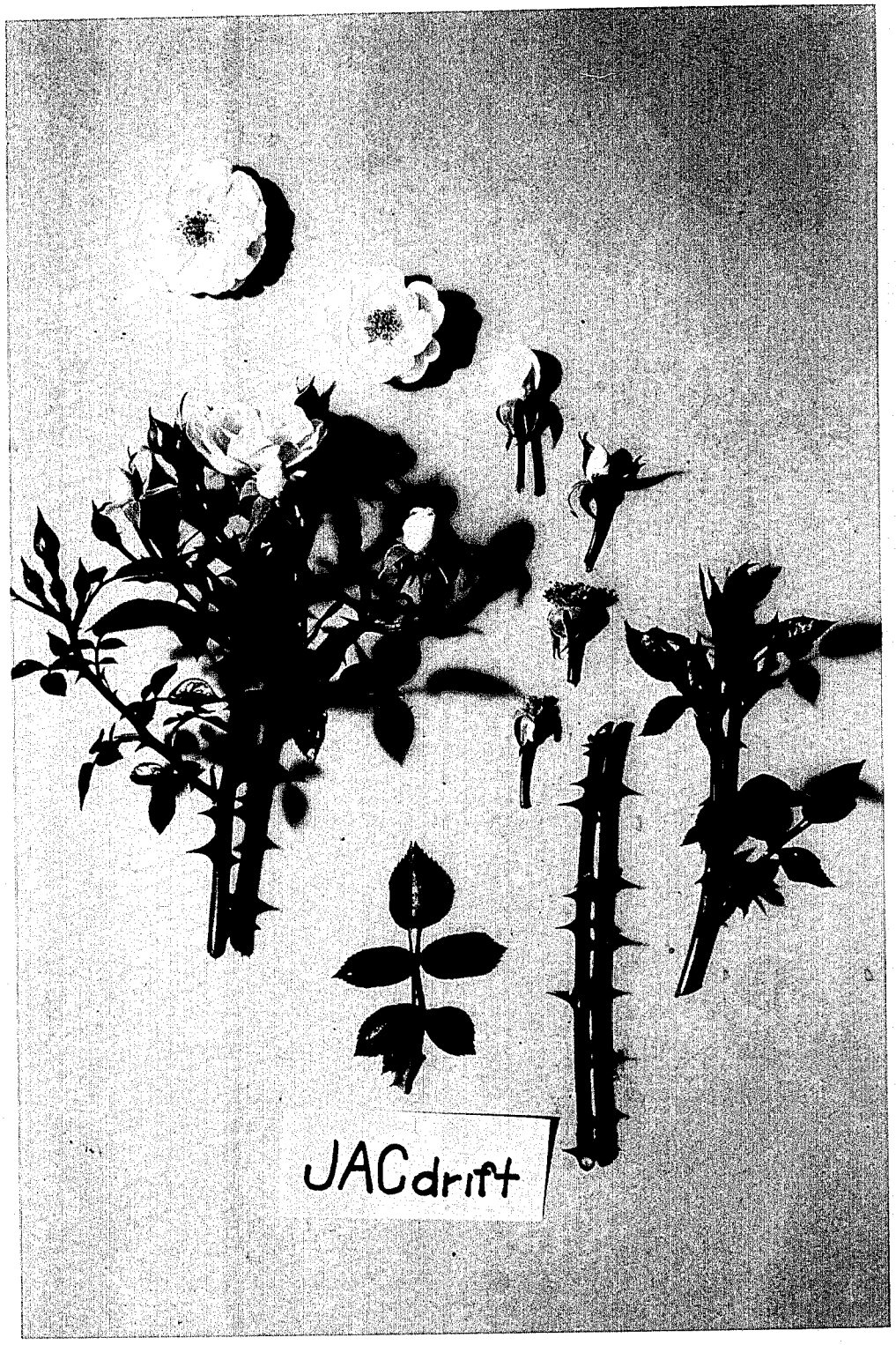
JACdrift